United States Patent [19]

Bach et al.

[11] Patent Number: 4,681,443
[45] Date of Patent: Jul. 21, 1987

[54] OPTICAL DETECTOR CELL

[75] Inventors: David T. Bach; Roger A. Gruenke, both of Wilmington, Del.; Herman W. Levin, Philadelphia, Pa.

[73] Assignee: E. I. Du Pont de Nemours and Company, Wilmington, Del.

[21] Appl. No.: 731,780

[22] Filed: May 8, 1985

[51] Int. Cl.[4] ............................................. G01N 1/10
[52] U.S. Cl. ........................................................ 356/246
[58] Field of Search ............... 356/246, 244, 317, 318, 356/339, 410, 73

[56] References Cited

U.S. PATENT DOCUMENTS

| | | | |
|---|---|---|---|
| 3,751,173 | 8/1973 | Sanz et al. | 356/246 |
| 3,985,441 | 10/1976 | Schoeffel et al. | 356/246 |
| 4,074,939 | 2/1978 | Rabl | 356/339 X |
| 4,283,141 | 8/1981 | Stockdale et al. | 356/246 |
| 4,330,206 | 5/1982 | Gausmann et al. | 356/246 |
| 4,440,497 | 4/1984 | Carey et al. | 356/246 |
| 4,455,089 | 6/1984 | Yeung et al. | 356/246 |

FOREIGN PATENT DOCUMENTS 0068287  6/1979  Japan ................................. 356/318

Primary Examiner—Davis L. Willis
Assistant Examiner—S. A. Turner

[57] ABSTRACT

An optical cell provides a measuring chamber which is L-shaped with an absorbance optical path lying along the horizontal leg of the L. A second optical path is provided transverse to the absorbance path and sized to permit the passage of radiation into the entire L-shaped chamber. The exit slit for the cell receives radiation from the entire vertical leg of the L and may serve as the entrance slit to a photometer.

12 Claims, 7 Drawing Figures

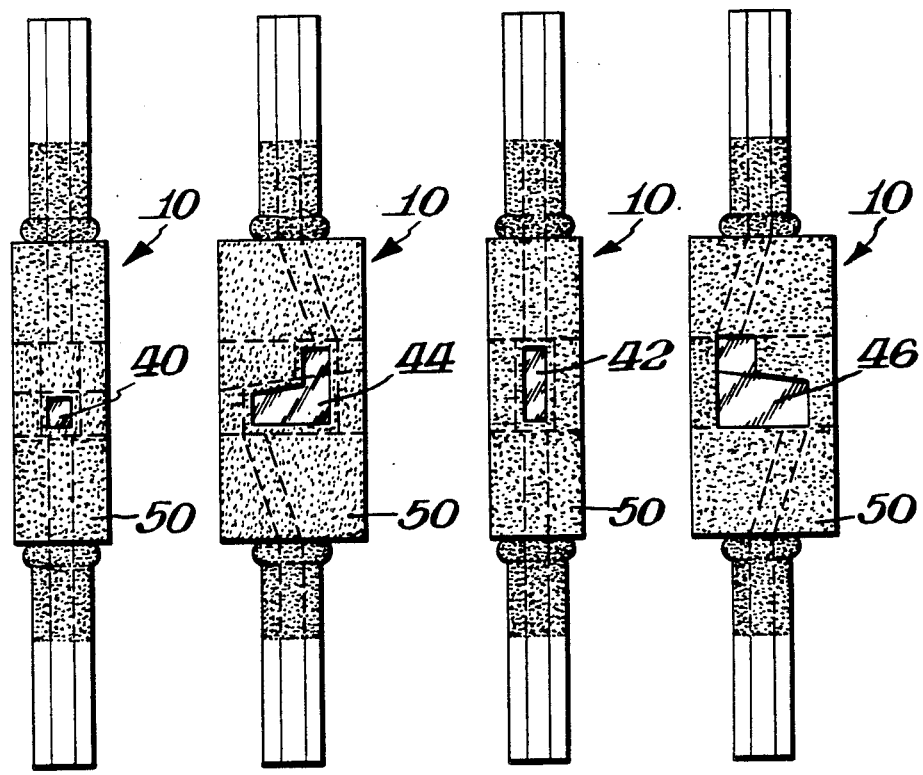

OPTICAL DETECTOR CELL

BACKGROUND OF THE INVENTION

This invention relates to optical detector cells and, more particularly, to optical flow cells capable of absorbance, turbidimetric, nephelometric and fluorescence measurements on a liquid.

Many analytical systems use optical detectors for measuring various physical properties of an analyte to be measured. These optical cells may be either fixed cells such as a cuvette or dynamic flow cells (in which a liquid is designed to flow through the cell). In both cases the liquid is subjected to radiation which is modified in some physical way depending on the constituents of the liquid. This modification is measured and is an indication of the presence or absence and quantity of a particular analyte.

Of the many optical cells designed for prior analytical systems, many have been designed to measure either the absorbance of a beam of radiation passing through a sample liquid or the turbidity of the sample liquid. Others, using nephelometric techniques measure the amount of radiation that is diffracted 90° to the angle of the original radiation or the fluorescence of the analyte being measured. Unfortunately many of these cells are not designed to measure more than the one physical property efficiently.

One of the cells which is typical of the prior art cells that are capable of measuring the absorbance or turbidity of the sample analyte is described in U.S. Pat. No. 4,330,206 issued May 18, 1982 assigned to Carl␣Zeiss-Stiftung. This patent describes a optical cuvette which is inherently self-cleaning of air or gas bubbles in liquid samples but again is limited only to the two types of measurements. Still another optical cell of the prior art is described in U.S. Pat. No. 4,440,497 issued Apr. 3, 1984 and assigned to Corning Glass Works. This particular cell is adapted to measure both absorbance and fluorescence of a sample using a single excitation source for the measurement of both. Separate detectors are used for measuring the respective absorbance and fluorescence properties, but the sample is exposed to the atmosphere and its volume is uncontrolled.

In addition to being able to measure using the same cell the four physical properties cited above, it would be highly desirable for a cell to have a maximum absorbance path length in order to achieve maximum sensitivity. To measure fluorescence using the same cell, the entrance slit of the photometer should be fully illuminated by and integrally coupled to the cells' fluorescing liquid. The fluorescent radiation from a sample cell normally is less than that produced by other physical phenomenon; hence, a larger portion of the sample must be excited by the exciting radiation in order to improve the signal to noise ratio of the detector. This creates a problem in that in order to build a cell having sufficient exposure of the sample liquid to the exciting radiation, the cell becomes oversized creating dead spaces so that the ability to measure flowing samples accurately is greatly decreased.

An additional factor in cell design is that the cell should have a small internal volume to satisfy the limited volume of samples that are available from the various analytical chemistries to which the sample is subjected. Finally, the cell should have an internal geometry which allows for relatively efficient wash-out of the samples. And lastly, but not least, the cell should be easy to fabricate and have as low a cost as possible.

SUMMARY OF THE INVENTION

An optical cell which overcomes many of the disadvantages of the prior art and which is capable of effecting absorbance, turbidimetric, nephelometric and/or fluorescence measurements on a liquid is constructed. For this purpose a cell having a measuring chamber for holding the liquid, a first access port for the chamber, and a first pair of entrance and exit optical walls lying along a first optical path through the chamber for accomodating the passage a radiation through the chamber is used. This cell is improved according to this invention to effect measurement of absorbance, turbidity, nephelometry and fluorescence by constructing the chamber to be L-shaped with the first optical path lying along the horizontal leg of the L, and to include a second pair of optical walls lying along a second optical path through the chamber transverse to the first path and sized to permit the passage of radiation through the entire L-shaped chamber, the exit one of the first pair of walls being sized to permit the passage of radiation from the entire vertical leg of the L which serves as the entrance slit to a photometer. This overcomes the difficulty normally encountered with the fluorescence and nephelometric modes due to decreased signal per unit volume of the liquid being measured. The cell of this invention provides a larger volume of liquid that produces the signal to be measured and fills the entrance slit of the photometer more effectively.

Preferably the entrance one of the first pair of walls is sized to permit the passage of radiation along the horizontal leg of the chamber. The first pair of walls is externally masked to provide an optical path having a cross-section width less than the cross-section width of the horizontal leg portion of the chamber. Also the exit one of the first pair of walls is externally masked to have a cross-section less than the cross-section of the vertical leg of the L portion of the chamber, thereby to define an aperture for a radiation detector. Preferably, the upper surface of the horizontal leg portion of the chamber inclines upwardly from the entrance wall thereby to prevent bubbles from being in the first optical path. The chamber may have a second port positioned at the top of the vertical leg of the L-shaped chamber portion for providing an exit for fluid in the chamber. The first port is positioned at the entrance wall of the horizontal leg of the chamber.

With a cell of this design many of the disadvantages of the prior art are overcome. Thus, with this type of a cell, absorbometric, turbidimetric, nephelometric, and fluorometric measurements can be made more efficiently using the same cell. The absorbance path length may be relatively long; in a typical case in the neighborhood of 5 millimeters. For fluorescence measurements, the entrance slit to the photometer is fully illuminated by and integrally coupled to the cells' fluorescence fluid which exits through the first optical path of the cell to a detector. The amount of liquid visible to the photometer entrance slit in the fluorescence or nephelometric modes is greater than the amount of fluid visible to the photometer in the absorbance or turbidimetric modes. Finally, the cell has a small internal volume, such that excessive sample volumes need not be used. The internal geometry of the cell allows for a very efficient wash-in and wash-out of the samples and the cell is easy to fabricate and is of low cost.

BRIEF DESCRIPTION OF THE DRAWINGS

The invention may be more fully understood from the following detailed description therof taken in connection with accompanying drawings which form a part of this application and in which:

FIG. 4 is an end elevation view of a complete optical cell viewing the masked exit aperture;

FIG. 5 is a side elevation view of the optical cell of FIG. 4 depicting the entrance aperture for the fluorescence radiation exciting source:

FIG. 6 is a side elevation view of the cell of FIG. 4 depicting the exit aperture for the fluorescence radiation exciting source; and FIG. 7 is a back elevation of the cell of FIG. 4 depicting the entrance aperture for the absorbance radiation.

DETAILED DESCRIPTION OF THE PREFERRED EMBODIMENTS

Figure 1:
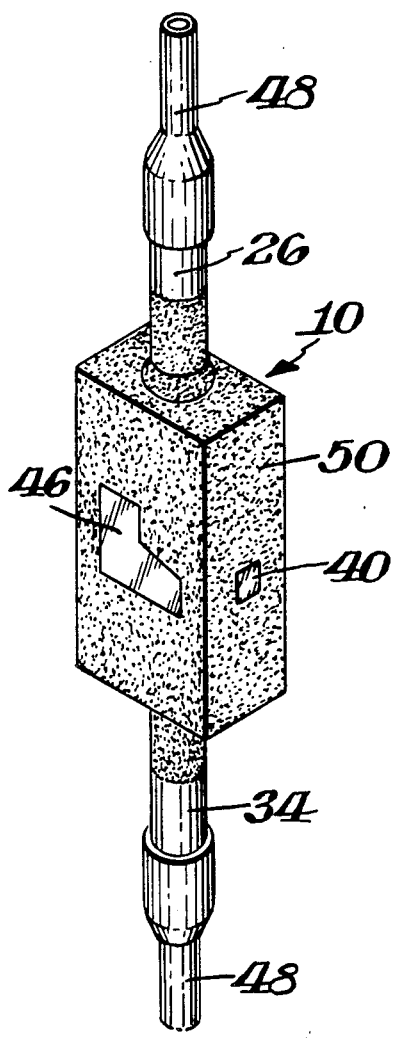
FIG. 1 is a pictorial view of an optical measuring cell constructed in accordance with this invention.
Figures 2, 3:
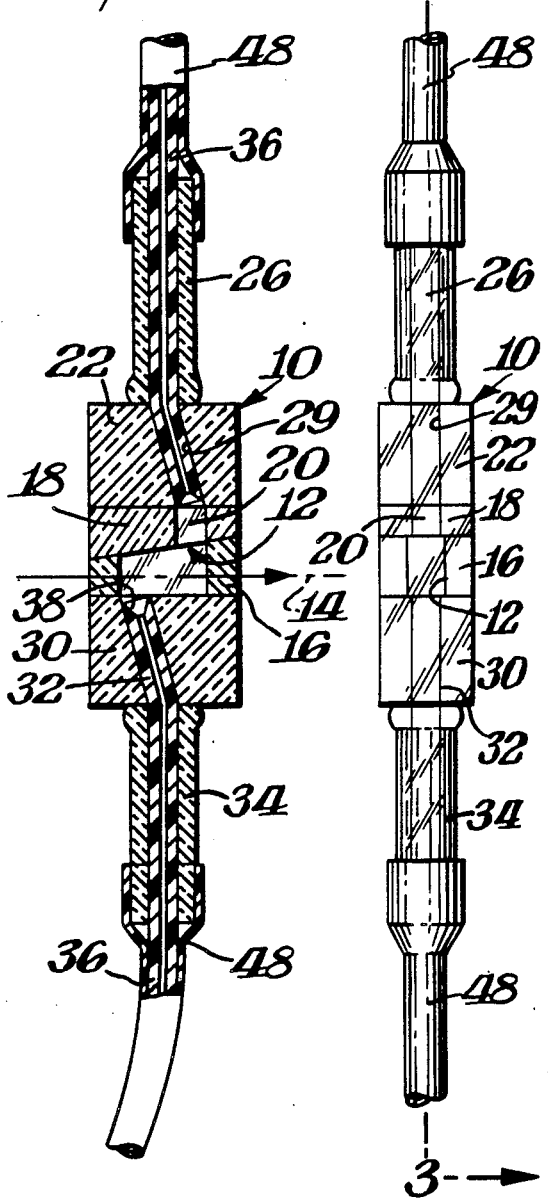
FIG. 2 is an end elevation view of the optical cell depicted in FIG. 1, but unmasked, viewing the optical wall containing the exit aperture for a radiation detection.
FIG. 3 is a cross-sectional elevation view of the cell depicted in FIG. 2 taken along the section line 3—3.

With reference to FIGS. 1 - 3, the structure of the optical measuring cell 10 of this invention may be seen. The cell 10 itself preferably is constructed of various pieces of quartz, i.e., spectrocell grade, S.U.B. fused silica. Alternatively it may be made of any optically transparent material such as glass, plastic and other materials known to those skilled in the art. In particular, the cell is configured to provide an L-shaped optical chamber 12 in which an absorbance measuring path denoted by the axis 14 lies along the horizontal leg of the L. The horizontal leg of the L may be formed by four flat slab-like pieces of quartz 16 fused together in a rectangular annulus-like shape to provide the horizontal leg portion of the L-shaped chamber 12. The vertical leg of the chamber 12 is formed by a second set of four pieces of quartz 18 fused together in an annulus-like rectangle to define the vertical leg portion 20 of the chamber. To complete the construction of the chamber 12, an upper block of quartz 22 having a bore 29 which communicates between the vertical leg portion 20 and the exterior of the cell. To facilitate the connection of the cell with tubing, a quartz tube 26 is fused to the block 22 to communicate with the bore 24.

Alternatively the chamber 12 can be formed of three pieces of quartz, one for each of the entrance and exit faces and one for the chamber itself. In this case, the L-shaped chamber is ground into the mid portion of a solid piece of quartz and the surfaces polished.

The lower portion of the cell 10 is similarly constructed with a lower block 30 defining a bore 32 which communicates with that portion of the horizontal leg of the L-shaped chamber forming the radiation entrance of the chamber 12. Similarly, a quartz tube 34 is fused to the lower end of the block 30 at the exit region of the bore 32. A suitable chemically inert plastic tubing 36 such as tetrafluoroethylene (teflon ®) is inserted through the tubing 34 and 36 to connect liquids to the cell. The upper end of the tubing 36 (as is also true for the lower end of the tubing 38) has its inside diameter tapered as at 39 to facilitate to the transition to the L-shaped chamber 12. Furthermore, the elements 18 forming the vertical leg portion 20 have their lower surfaces tapered upwardly at a approximately a 5° angle to facilitate the escape of air and other debris entering the cell. The upper surfaces of the elements 16 forming the horizontal leg portion are tapered similarly to complement the taper of the elements 18.

To complete the construction of the cell, the exterior of all the quartz elements comprising the cell are coated with, as by evaporation, chromium or similar optically opaque mirror like material. This masking coating is applied to the entire exterior of the cell with the exception of those regions that provide entrance and exit windows for the absorbance and turbidimetric excitation radiation on the one hand and for the fluorescence and nephelometric exciting source on the other hand. Thus, as may be seen in FIG. 7, a small entrance window 40 is positioned along the axis 14 (FIG. 3) to permit the source of absorbance, etc., radiation to pass along the horizontal leg of the L and through the lower half of an exit window or aperture 42 (FIG. 4). The exit aperture is narrower than the entrance window 40. For the fluorescence excitation, an L-shaped entrance window 44 is provided as seen in FIG. 5 so as to permit the entire volume of the L-shaped chamber 12 (FIG. 3) to be radiated. Similarly, a fluorescence exit window 46, as seen in FIG. 6, is provided which is slightly larger than the entrance window 44. The fluorescence exit window may be mirrored to enhance fluorescence excitation. In each case, the windows are slightly less in cross-section than the corresponding cross-section of the chamber through which the radiation is to pass. This is done to prevent the radiation from striking the walls of the chamber and creating multiple reflections therein. Finally, a shrink tubing 48 (FIG. 3) is placed over the tubing 36, 38 and quartz tubing studs 34, 26 to hold the tubing 36, 38 in position.

The cell thus constructed can be made small in internal volume and yet as described provides a relatively long path for the absorbance radiation along the axis 14. The exit window 42 may function as the entrance slit of a photometer in which the cell of this invention is used. A path for the fluorescence excitation is provided through the fluorescence windows 44 and 46 that excites a still larger volume of the sample liquid than is subjected to the absorbance radiation. This is because both legs of the "L" are excited and this constitutes the entire volume of the cell. The liquid in the cell so excited with fluorescence radiation fluoreses and the resulting fluorescence radiation exits through the entire cross-section of the exit window 42 (FIG. 4). This illumination of the entire volume of the cell results in a greater fluorescence illumination, which is allowed to pass through window 42 to a detector, than would normally occur. In the event an array detector is used, the exit window 42 may be sized to permit the illumination to strike the appropriate elements of the array. For nephelometry the illumination also passed through the fluorescence window 44. The resulting 90° refractions pass out through the exit window 42. Turbiditry measurements are accomplished along the axis 14. As may be seen, the flow channel is designed to be easily flushed and to remove all air bubbles and other material. There are few dead spaces and those that exist are dictated only by the optical needs of the cell. It should be noted that the chamber 12 is rectangular in cross-section and has a small internal volume. The volume being only sufficient to provide the optical path lengths necessary for efficient operation of the detector.

What is claimed is:

1. In an optical detector cell for effecting measurements on a liquid, the cell having a measuring chamber for holding the liquid, a first access port for the chamber, a first pair of entrance and exit optical walls lying along a first optical path through the chamber for accommodating the passage of radiation through the chamber, a second pair of optical walls lying along a second optical path transverse to the first path, the improvement for also effecting nephelometric and fluorescence measurements on a liquid in the cell wherein the chamber:

is L-shaped with the first optical path lying along the horizontal leg of the L and the exit optical wall is adjacent the upright leg of the L, a second pair of walls are sized to permit the passage of radiation through substantially all of the L-shaped chamber, the exit one of first pair of walls being sized to permit the passage of radiation from substantially all of the vertical leg of the L, whereby the fluorescent volume of the chamber capable of passing through the first exit wall is larger than the volume of the chamber lying on the first optical path.

2. The detector cell set forth in claim 1 wherein the entrance one of the first pair of walls is flat and sized to permit the passage of radiation along the horizontal leg of the chamber.

3. The detector cell set forth in claim 2 wherein each of the first pair of walls is masked to provide an optical path having a cross-section width less than the cross-section width of the horizontal leg portion of the cell.

4. The detector cell set forth in claim 3 wherein the exit one of the first pair of walls is masked to have a cross-section less than the cross-section of the vertical leg of the L portion of the chamber, thereby to define an aperture for a radiation detector.

5. The detector cell set forth in claim 4 wherein the upper surface of the horizontal leg portion of the chamber inclines upwardly from the entrance wall, thereby to prevent bubbles from being in the first optical path.

6. The detector cell set forth in claim 5 wherein the chamber is formed totally of quartz.

7. The optical detector cell set forth in claim 1 wherein each of the first pair of walls is masked to provide an optical path having a cross-section width less than the cross-section width of the horizontal leg a portion of the cell.

8. The optical detector cell set forth in claim 1 wherein the exit one of the first pair of walls is masked to have a cross-section less than the cross-section of the vertical leg of the L portion of the chamber, thereby to define an aperture for a radiation detector.

9. The optical detector cell set forth in claim 1 wherein the chamber has a second port positioned at the top of the vertical leg of the L chamber portion for providing an exit for fluid in the chamber and the first port is positioned at the entrance wall of the horizontal leg of the chamber.

10. The optical detector cell set forth in claim 9 wherein the entrance one of the first pair of walls is sized to permit the passage of radiation along the horizontal leg of the chamber.

11. The optical detector cell set forth in claim 10 wherein each of the first pair of walls is masked to provide an optical path having a cross-section width less than the cross-section width of the horizontal leg portion of the cell.

12. The optical detector cell set forth in claim 9 wherein the vertical and horizontal leg portions of the chamber are rectangular in cross-section.

* * * * *